(12) United States Patent
Imai et al.

(10) Patent No.: US 8,129,122 B2
(45) Date of Patent: Mar. 6, 2012

(54) METHOD OF PREDICTING METASTASIS OF ORAL CAVITY CANCER INTO CERVICAL LYMPH NODE AND DIAGNOSIS KIT TO BE USED IN THE PREDICTION

(75) Inventors: Takashi Imai, Chiba (JP); Mayumi Iwakawa, Chiba (JP); Hitoshi Shibuya, Chiba (JP); Masahiko Miura, Chiba (JP); Ryoichi Yoshimura, Chiba (JP); Hiroshi Watanabe, Chiba (JP)

(73) Assignee: National Institute of Radiological Sciences, Chiba-Shi, Chiba (JP)

( * ) Notice: Subject to any disclaimer, the term of this patent is extended or adjusted under 35 U.S.C. 154(b) by 230 days.

(21) Appl. No.: 12/310,331

(22) PCT Filed: Mar. 30, 2007

(86) PCT No.: PCT/JP2007/057151
§ 371 (c)(1),
(2), (4) Date: Feb. 20, 2009

(87) PCT Pub. No.: WO2008/026340
PCT Pub. Date: Mar. 6, 2008

(65) Prior Publication Data
US 2009/0317813 A1    Dec. 24, 2009

(30) Foreign Application Priority Data
Sep. 1, 2006   (JP) ................. 2006-237793

(51) Int. Cl.
*C12Q 1/68* (2006.01)
*C07H 21/04* (2006.01)
*C12N 15/11* (2006.01)
*C12N 15/12* (2006.01)

(52) U.S. Cl. ................... 435/6.14; 536/24.31

(58) Field of Classification Search .............. None
See application file for complete search history.

(56) References Cited

OTHER PUBLICATIONS

Amersham Biosciences, CodeLink human whole genome bioarray, 63-0054-47/Rev. A/2004 (2004).*

Shibuya et al., "Brachytherapy for stage I & II oral tongue cancer: An analysis of past cases focuing on control and complications", 1993, Int. J. Radiation Oncology Biol. Phys., vol. 26, pp. 51-58.

Nakagawa et al., "Neck node metastasis after successful brachytherapy for early stage tongue carcinoma", 2003, Radiotherapy and Oncology , vol. 68, pp. 129-135.

Katayama et al., "Expressions of Matrix Metalloproteinases in Early-Stage Oral Squamous Cell Carcinoma as Predictive Indicators for Tumor Metastases and Prognosis", 2004, Clinical Cancer Research, vol. 10, pp. 634-640.

Myo et al., "Cyclin D1 Gene Numerical Aberration is a Predictive Marker for Occult Cervical Lymph Node Metastasis in TNM Stage I and II Squamous Cell Carcinoma of the Oral Cavity", 2005, American Cancer Society, vol. 104, No. 12, pp. 2709-2716.

Chung et al., "Molecular classification of head and neck squamous cell carcinomas using patterns of gene expression", Cancer Cell, 2004, vol. 5, pp. 489-500.

O'Donnell et al., "Gene expression signature predicts lymphatic metastasis in squamous cell carcinoma of the oral cavity", 2005, Oncogene, 2005, vol. 24, No. 7, pp. 1244-1251.

Roepman et al., "An expression profile for diagnosis of lymph node metastases from primary head and neck squamous cell carcinomas", 2005, Nature Genetics, vol. 37, No. 2, pp. 182-186.

M. Masuda, et al., "Decreased CD44H Expression in Early-Stage Tongue Carcinoma Associates With Late Nodal Metastases Following Interstitial Brachytherapy"; Head and Neck, Oct. 2000, pp. 662-665.

* cited by examiner

*Primary Examiner* — James Martinell
(74) *Attorney, Agent, or Firm* — Squire Sanders (US) LLP (57) ABSTRACT

A method for objectively predicting possibility of metastasis to a cervical lymph node in an early stage for an individual case diagnosed as an oral cavity cancer, and a diagnosis kit to be used in the prediction are provided. The method includes a step of assaying expression amounts of metastasis prediction genes in which the expression amounts are changed between a metastasis group and a non-metastasis group, with respect to a sample collected from a primary legion of the oral cavity cancer. Further, the method includes a step of predicting the possibility of the metastasis by comparing the expression amounts of the metastasis gene group with the expression amounts of the metastasis prediction genes in a metastasis group and/or a non-metastasis group. Herein, the metastasis prediction gene group includes two genes MSR1 (NM_138716.1) and RET (M31213.1).

8 Claims, 2 Drawing Sheets

METHOD OF PREDICTING METASTASIS OF ORAL CAVITY CANCER INTO CERVICAL LYMPH NODE AND DIAGNOSIS KIT TO BE USED IN THE PREDICTION

BACKGROUND OF THE INVENTION

1. Field of the Invention

The present invention relates to a method for predicting metastasis of an oral cavity cancer to a cervical lymph node and a diagnosis kit to be used in the prediction.

2. Description of the Related Art

An oral cavity cancer is a malignant tumor generated in an oral cavity. 90% and more of the oral cavity cancer is squamous epithelium carcinoma generated from oral mucosa. A surgery therapy and a radiation therapy are used as treatment for the oral cavity cancer. Hereby, relatively higher healing rates are expected. Actually, a region management ratio of the oral cavity cancer in Stage I and Stage II according to a UICC classification (Union International Contre Cancer) (in 2002) is in a range of 80% to 90%.

Metastasis to a cervical lymph node is cited to be an important prognostic factor to predict how the oral cavity cancer progresses after treatment.

The cervical lymph node plays a role of such a so called checkpoint of preventing cancer cells which flow in lymph from an oral cavity primary lesion from disseminating to a whole body. By capturing cancer cells, the cervical lymph node has a character that it swells at the position where the cancer cells are captured. In many cases, the swelling cervical lymph node is surgically extracted by an operation. Herein, it is suggested that the number of metastasis lymph nodes which are pathologically determined after surgery and whether or not cancer cells develop outside a membrane covering the lymph node are directly related to prognosis thereof.

Therefore, if the metastasis of the oral cavity cancer to the cervical lymph node for an oral cavity cancer patient is detected in early stages, improvement for the prognosis of the oral cavity cancer can be expected. For this reason, methods for predicting the metastasis to the cervical lymph node before treatment have been developed. Hereinafter, two conventional methods for predicting the metastasis of the oral cavity cancer to the cervical lymph node will be explained.

A first prediction method is a method of predicting metastasis by a clinical classification of cancers. For example, according to the clinical classification, tumor types of a lingual cancer included in the oral cavity cancer are classified into three types: superficial, outward, and inward types. Herein, it is known that an inward tumor metastasizes more easily than an outward tumor (for example, refer to Non Patent Documents 1 to 3, described below). That is, according to the first prediction method, a metastasis occurring rate to the cervical lymph node is estimated by the clinical classification of cancers.

A second prediction method is a method of predicting the metastasis by molecular pathological retrieving. Studies predicting metastasis for a case in which whether cancers metastasize or not is unknown, have been developed by analyzing a gene expression state of a cancer gene, a cancer-inhibiting gene, and genes related to a signaling factor and a cell adhesion. Recently it has become possible to exhaustively analyze a gene expression in a post-genome era. Studies using a microarray technology have been developed (for example, refer to Non-Patent Documents 4 to 8).

However, the first prediction method only shows a stochastically occurring rate on the metastasis to the cervical lymph node for a group of symptoms. Accordingly, there is a problem that the method does not predict the possibility of the metastasis to the cervical lymph node for an individual symptom.

Further, the second prediction method is expected to predict the possibility of the metastasis to the cervical lymph node for an individual symptom. However, the method has not been clinically applied to date.

More specifically, if a protein expression is determined by an immunogenic histological method, quantitative determination with reproducibility is difficult due to intrinsically subjective valuation property of the method, as described in Non-Patent Document 4.

Further, Non-Patent Document 5 describes analyses on relationships among a protein and mRNA expression of Cyclin D1 and a metastatic or prognostic progress; the relationships having been suggested heretofore, and the analyses are performed by using a FISH method having a high sensitivity for a gene amplification. According to the document, a high predicting rate that indicates a correct diagnosis rate of about 80% is achieved. However, it is suggested that the prediction method needs time and a labor cost because technique is required for the FISH method in itself and complicated processes are required to determine occurrence of a gene amplification (condition to determine presence of a CCND1 expression is that three and more signals are observed in 20% and more nuclei in 200 interphase cells). Accordingly, the complicated processes to the data determination together with the high costs required for the method may prevent the clinical application thereof.

Non-Patent Documents 6, 7 and 8 are articles in which a microarray technology is used.

According to Non-Patent Document 7, since the number of cases of a test group is only four, the number is too few for data to be authenticated sufficiently. Further, O'Donnell et al. perform a basic analysis on a comparison between a primary lesion and a metastatic lesion, and do not supply the clinical data on subjects. Therefore, it is difficult to apply their data to a clinical use.

According to Non-Patent Documents 6 and 8, Chung and Roepman et al. perform prophylactic cervical total dissection, chemotherapy and/or postoperative radiotherapy for treatment of a primary lesion. Although it is desirable to take a "wait and see policy" for a cervix to detect an occurrence of metastasis to a lymph node, the policy is not taken in the study. Further, a scoring method for the data is not defined clearly.

Therefore, it is desired to have a method for objectively predicting possibility of metastasis to a lymph node in an early stage for an individual case diagnosed as an oral cavity cancer.

[Non-Patent Document 1] Shibuya H., Hoshina M., Takeda M., Matsumoto S., Suzuki S., Okada N., "Brachytherapy for stage I and II oral tongue cancer: An analysis of past cases focusing on control and complications." Int J Radiat Oncon Biol Phys 1993, 26, 51-8;

[Non-Patent Document 2] Nakagawa, T., Shibuya H., Yoshimura R., Miura M., Okada N., Kishimoto S., Amagasa M., Omura K., "Neck node metastasis after successful brachytherapy for early stage tongue carcinoma." Radiotherapy and Oncology 2003, 68, 129-135;

[Non-Patent Document 3] the Scientific Committee of the Japan Society for Oral Tumor ed., Guideline for treatment of Lingual Cancers, Oral Tumor, 2005, 17 (1), 13-85.

[Non-Patent Document 4] Katayama A., Bandoh N., Kishibe K., Takahara M., Ogino T., Nonaka S., Harubuchi Y., "Expressions of matrix metalloproteinases in early-stage oral squamous cell carcinoma as predictive indicators for tumor metastases and prognosis." Clinical Cancer Res 2004, 10, 634-640;

[Non-Patent Document 5] Myo K., Uzawa N., Miyamoto R., Sonoda I., Yuki Y., Amagasa T., "Cyclin D1 gene numerical aberration is a predictive marker for occult cervical lymph node metastasis in TNM stage I and II squamous cell carcinoma of the oral cavity." Cancer 2005, 2709-2716;

[Non-Patent Document 6] Chung C., Parker J., Karaca G., Wu J., Funkhouser W., Moore D., Butterfoss D., Xiang D., Zanation A., Yin X., Shockley W., Weisser M., Dressler L., Shores C., Yarbrough W., Perou C., "Molecular classification of head and neck squamous cell carcinomas using patterns of gene expression." Cancer Cell 2004, 5, 189-500;

[Non-Patent Document 7] O'Donnell R., Kupferman M., Wei S., Singhal S., Weber R., O'Malley B., Cheng Y., Putt M., Feidman M., Ziober B., Muschel R., "Gene expression signature predicts lymphatic metastasis in squamous cell carcinoma of the oral cavity." Oncogene 2005, 24, 1244-1251;

[Non-Patent Document 8] Reopman P., Wessels F., Kettelarij N., Kemmeren P., Miles A., Lijnzaad P., Tilanus M., Koole R., Hordijk G., Vliet P., Reinders M., Slootweg P., Holstege F., "An expression profile for diagnosis of lymph node metastases from primary head and neck squamous cell carcinomas." Nature Genetics 2005, 37, 182-186.

SUMMARY OF THE INVENTION

It is an object of the present invention to provide a prediction method for metastasis of an oral cavity cancer to a cervical lymph node and a diagnosis kit for predicting the metastasis of the oral cavity cancer to the cervical lymph node.

[1] The method for predicting the metastasis of the oral cavity cancer to the cervical lymph node according to the present invention comprises steps of: assaying expression amounts of a metastasis prediction gene group in which the expression amounts are changed between a metastasis group including a case indicating the metastasis of the oral cavity cancer to the lymph node and a non-metastasis group including a case indicating no metastasis, with respect to a sample collected from a primary lesion of the oral cavity cancer; and predicting possibility of the metastasis of the oral cavity cancer to the cervical lymph node by comparing the expression amounts of the metastasis prediction gene group with expression amounts of the metastasis prediction genes in the metastasis group and/or the non-metastasis group. Herein, the metastasis prediction gene group includes two genes: MSR1 (NM_138716.1) and RET (M31213.1).

[2] The metastasis prediction gene group can further be composed of a gene: FARP1 (CD675885.1)

[3] The metastasis prediction gene group can furthermore be composed of at least one of 16 genes: ARG1 (NM_000045.2), FARP1 (NM_005766.2), H19 (R83431.1), NULL (BC019018.2), NULL (AW820586.1), NULL (H08012.1), MUC15 (NM_145650.2), HHLA2 (NM_007072.2), SGCD (NM_172244.2), SFRP4 (NM_003014.2), ALOX12 (NM_000697.1), LOC146429 (AL137382.1), PDZRN3 (AL137307.1), NCAM1 (AV702977.1), WNT11 (NM_004626.2), and SORCS2 (NM_020777.1).

[4] The metastasis prediction gene group can further be composed of all of the 16 genes: ARG1 (NM_000045.2), FARP1 (NM_005766.2), H19 (R83431.1), NULL (BC019018.2), NULL (AW820586.1), NULL (H08012.1), MUC15 (NM_145650.2), HHLA2 (NM_007072.2), SGCD (NM_172244.2), SFRP4 (NM_003014.2), ALOX12 (NM_000697.1), LOC146429 (AL137382.1), NCAM1 (AV702977.1), WNT11 (NM_004626.2), and SORCS2 (NM_020777.1).

[5] According to the present invention, the diagnosis kit for predicting the metastasis of the oral cavity cancer to the cervical lymph node includes two kinds of oligonucleotides which can specifically hybridize two gene sequences of MSR1 (NM_138716.1) and RET (M31213.1).

[6] The diagnosis kit for predicting the metastasis of the oral cavity cancer to the cervical lymph node can further include an oligonucleotide which can specifically hybridize a gene sequence of FARP1 (CD675885.1).

[7] The diagnosis kit for predicting the metastasis of the oral cavity cancer to the cervical lymph node can further include oligonucleotides which can specifically hybridize at least one sequence of 16 genes: ARG1 (NM_000045.2), FARP1 (NM_005766.2), H19 (R83431.1), NULL (BC019018.2), NULL (AW820586.1), NULL (H08012.1), MUC15 (NM_145650.2), HHLA2 (NM_007072.2), SGCD (NM_172244.2), SFRP4 (NM_003014.2), ALOX12 (NM_000697.1), LOC146429 (AL137382.1), PDZRN3 (AL137307.1), NCAM1 (AV702977.1), WNT11 (NM_004626.2), and SORCS2 (NM_020777.1).

[8] The diagnosis kit for predicting the metastasis of the oral cavity cancer to the cervical lymph node can further include 16 kinds of oligonucleotides which can specifically hybridize all of the sequences of 16 genes: ARG1 (NM_000045.2), FARP1 (NM_005766.2), H19 (R83431.1), NULL (BC019018.2), NULL (AW820586.1), NULL (H08012.1), MUC15 (NM_145650.2), HHLA2 (NM_007072.2), SGCD (NM_172244.2), SFRP4 (NM_003014.2), ALOX12 (NM_000697.1), LOC146429 (AL137382.1), PDZRN3 (AL137307.1), NCAM1 (AV702977.1), WNT11 (NM_004626.2), and SORCS2 (NM_020777.1).

According to the present invention, the following effects can be expected.

According to the present invention, the method for predicting the metastasis of the oral cavity cancer to the cervical lymph node can objectively predict in an early stage the possibility of the metastasis to the cervical lymph node for an individual case diagnosed as the oral cavity cancer.

Further, according to the present invention, the diagnosis kit for predicting the metastasis of the oral cavity cancer to the cervical lymph node can objectively predict in the early stage the possibility of the metastasis to the cervical lymph node for an individual case diagnosed as the oral cavity cancer.

The above-mentioned features and effects of the present invention together with additional effects and features will be more evident by detailed explanation of explanatory and non-restricted embodiments of the present invention which are described later with reference to attached drawings.

DETAILED DESCRIPTION OF THE PREFERRED EMBODIMENTS

Hereinafter, the best mode for carrying out the present invention (hereinafter, described as preferred embodiment) will be explained in detail appropriately referring to drawings.

(Metastasis Prediction Gene Group)

The present invention is achieved based on a discovery by the present inventors that expression amounts of 19 kinds of genes (metastasis prediction genes) shown in Table 1 hereinafter, that is, expression amounts of mRNAs transcribed from the genes are changed with a statistically significant difference between a metastasis group including a case in which an oral cavity cancer metastasizes to a cervical lymph node and a non-metastasis group with no metastasis, with respect to a sample collected from a primary legion of the oral cavity cancer.

Here, "metastasis prediction gene group" according to the embodiment is a group consisting of a plurality of genes out of 19 genes (metastasis prediction genes) shown in Table 1.

(Method for Predicting Metastasis of Oral Cavity Cancer to Cervical Lymph Node)

A metastasis prediction method of the embodiment includes steps of: assaying expression amounts of a metastasis prediction gene group; and predicting possibility that an oral cavity cancer metastasizes to a cervical lymph node by statistically comparing expression amounts of the metastasis prediction gene group with expression amounts of the metastasis prediction genes in a metastasis group and/or a non-metastasis group.

Firstly, the step of assaying the expression amounts of the metastasis prediction gene group will be explained.

A sample for assaying the expression amounts of the metastasis prediction gene group is collected from a primary legion of a subject diagnosed as the oral cavity cancer. For example, the sample is collected from a primary legion before treatment such as a small radiation source therapy. Here, a subject from which a sample is collected is explained supposing the subject as a human in the embodiment. Alternatively, a non-human animal such as a mouse, a dog and a monkey can be included as a subject.

TABLE 1

List of 19 candidate genes for predicting N status.

| Rank order | NCBI accession no. | Symbol | Gene discription | Permutational p-value | Mean ratio (N + class)/ (N − class) |
|---|---|---|---|---|---|
| 1 | NM_138716.1 | MSR1 | macrophage scavenger receptor 1 (MSR1), transcript variant SR-AIII | 0.0003 | 2.2 |
| 2 | M31213.1 | RET | papillary thyroid carcinoma-encoded protein mRNA | 0.0004 | 3.2 |
| 3 | CD675885.1 | FARP1 | fs29d06y1 Human Lens cDNA (Normalized): fs cDNA clone fs29d06 5' | 0.0007 | 2.1 |
| 4 | NM_000045.2 | ARG1 | arginase, liver (ARG1) | 0.0010 | 0.4 |
| 5 | NM_005766.2 | FARP1 | FERM, RhoGEF (ARHGEF) and pleckstrin domain protein 1 (chondrocyte-derived) (FARP1), transcript variant 1 | 0.0016 | 2.0 |
| 6 | R83431.1 | H19 | yp82g02r1 Soares fetal liver spleen 1NFLS cDNA clone IMAGE: 193970 5' | 0.0037 | 2.1 |
| 7 | BC019018.2 | NULL | cDNA clone IMAGE: 3941904 | 0.0045 | 2.0 |
| 8 | AW820586.1 | NULL | QV2-ST0298-240200-063-d06 ST0298 Homo sapiens cDNA | 0.0054 | 2.1 |
| 9 | NM_007072.2 | HHLA2 | HERV-H LTR-associating 2 (HHLA2) | 0.0056 | 0.5 |
| 10 | NM_172244.2 | SGCD | sarcoglycan, delta (35 kDa dystrophin-associated glycoprotein) (SGCD), transcript variant 2 | 0.0057 | 2.4 |
| 11 | NM_003014.2 | SFRP4 | secreted frizzled-related protein 4 (SFRP4) | 0.0065 | 3.1 |
| 12 | NM_000697.1 | ALOX12 | arachidonate 12-lipoxygenase (ALOX12) | 0.0078 | 0.4 |
| 13 | AL137382.1 | LOC146429 | mRNA; cDNA DKFZp434L1226 (from clone DKFZp434L1226) | 0.0079 | 0.5 |
| 14 | AL137307.1 | PDZRN3 | mRNA; cDNA DKFZp586L2217 (from clone DKFZp586L2217) | 0.0082 | 0.3 |
| 15 | AV702977.1 | NCAM1 | ADB cDNA clone ADBCVD08 5' | 0.0083 | 2.2 |
| 16 | NM_004626.2 | WNT11 | wingless-type MMTV integration site family, member 11 (WNT11) | 0.0085 | 2.5 |
| 17 | NM_020777.1 | SORCS2 | sortilin-related VPS10 domain containing receptor 2 (SORCS2) | 0.0086 | 3.2 |
| 18 | NM_145650.2 | MUC15 | mucin 15 (MUC15) | 0.0091 | 0.4 |
| 19 | H08012.1 | NULL | y191b08r1 Soares infant brain 1NIB cDNA clone IMAGE: 45474 5' | 0.0092 | 6.9 |

The top 19 gene sets were listed as the rank-order of permutational p-values that were <0.01.

In Table 1, "Rank order" refers to an order ranking 19 kinds of metastasis prediction genes in a suitable sequence for predicting the metastasis of the oral cavity cancer. Further, as described later, preferably genes (MSR1, RET and FARP1) having the rank order of 1 to 3, more preferably genes (MSR1 and RET) having the rank order of 1 and 2 are used for predicting the metastasis of the oral cavity cancers.

"NCBI accession no." is a number given to each metastasis prediction gene in a database of the National Center for Biotechnology Information in which each metastasis prediction gene is registered and disclosed. A "symbol" is a name of each metastasis prediction gene. A "gene description" is an explanation of an outline of each metastasis prediction gene. A "permutation p-value" refers to a p value in a permutation test which is carried out to select 19 genes as shown in Examples described later. A "mean ratio (N+ class)/(N− class) refers to a ratio of an expression amount between a metastasis group (N+ class) and a non-metastasis group (N− class) in each metastasis prediction gene.

Further, a method for storing the collected sample can be any method in which mRNAs are stably stored, and it is not specifically limited. For example, a biopsy tissue can be directly used for steps shown hereinafter. A collected biopsy tissue once stored with being embedded in paraffin can be used for the steps shown hereinafter.

A method for extracting mRNAs from biological components (tissue and cell) generally used by those skilled in the art can be suitably utilized as a method for extracting mRNAs from the collected tissues. The method for extracting mRNAs from the biological components (tissue and cell) includes methods such as phenol extraction, ethanol precipitation, and an oligo dT column method. Additionally, RNA extraction kits provided by vendors on the market can be suitably utilized.

A method for assaying expression amounts of genes generally used by those skilled in the art can be suitably utilized as a method for assaying the expression amounts of the metastasis prediction gene group. The method for assaying the gene expression amounts includes, for example, a method based on hybridization such as a microarray and Northern blot, and a method based on a primer extension such as RT-PCR (Reverse transcriptase-polymerase chain reaction).

Herein, an expression amount of any portions of each gene may be assayed, if the expression amount of the metastasis prediction gene group can be assayed. For example, an expression amount of an mRNA corresponding to the whole length sequence of the gene may be assayed, or an expression amount of a portion thereof may be assayed. Further, for example, an expression amount of an hnRNA may be assayed and an expression amount of an mRNA matured by splicing may be assayed.

Base sequences used for a primer or a probe which the assay method uses are capable of specifically hybridizing respective mRNAs of the metastasis prediction gene group which is contained in the collected sample. For example, the base sequence may hybridize the whole length sequence of the metastasis prediction gene or its portion length sequence. Further, the base sequence may hybridize an mRNA including a cap sequence and a polyadenyl sequence, or an mRNA without including such a sequence. In other words, according to a method for assaying the expression amount, a suitable base sequence is appropriately selected as a primer or a probe. The primer and the probe do not need to have a specific base sequence. What is needed is only that whether the gene is expressed or not can be confirmed.

Here, if a diagnosis kit containing a primer or a probe (oligonucleotide) capable of specifically hybridizing mRNAs of the above metastasis prediction gene group is used, a method for predicting metastasis of an oral cavity cancer to a lymph node according to the present invention can be easily carried out. Herein, an "oligonucleotide" refers to a primer or a probe satisfying the conditions hereinbefore, and does not intend to specifically define the number of bases thereof. Detailed explanation of the diagnosis kit will be described later.

Next, will be explained a prediction step in which possibility that the oral cavity cancer metastasizes to the cervical lymph node is predicted by statistically comparing the expression amounts of the metastasis prediction gene group with the expression amounts of the metastasis prediction genes in the metastasis group and/or the non-metastasis group.

A statistical method which is generally used by those skilled in the art to evaluate a difference between two groups can be suitably applied to the statistical method used in this step, for example, a nearest mean classifier (NMC) method, a diagonal linear discriminant classifier (DLDC) method, a k-nearest neighbor predictor (k-NN) method, and a linear support vector machine (linSVC) method (refer to Wesels L. A., Reinders M. J., Hart A. M., et al.; A protocol for building and evaluating predictors of disease state based on microarray data, Bioinformatics 21, 3755-3762, 2005). However, the statistical method used in the step is not specifically limited to these methods.

The method used in the step includes at least a step in which whether or not the oral cavity cancer of an assay target metastasizes to the cervical lymph node is determined. This determination is made by processes of: comparing the measured expression amounts with the expression amounts of the metastasis group and/or the expression amounts of the non-metastasis group using the expression amounts of the metastasis prediction gene group as an indicator; and evaluating that which of the expression amounts of the metastasis group or the expression amounts of the non-metastasis group, the measured expression amounts of the metastasis prediction gene group are close to. Herein, the step can include a process in which whether or not the oral cavity cancer of the assay target metastasizes to the cervical lymph node is determined, by setting a predetermined threshold value and evaluating whether the assayed expression amount of the metastasis prediction gene is over the threshold value or under the value.

(Diagnosis Kit for Predicting Metastasis of Oral Cavity Cancer to Cervical Lymph Node)

As mentioned above, the diagnosis kit for predicting the metastasis of the oral cavity cancer to the cervical lymph node according to the embodiment comprises a primer and a probe (oligonucleotide) capable of specifically hybridizing genes respectively which are listed in the metastasis prediction gene group shown in Table 1.

For example, the diagnosis kit comprises 2 kinds of oligonucleotides capable of specifically hybridizing 2 gene sequences of MSR1 (NM_138716.1) and RET (M31213.1), respectively.

Further, for example, the diagnosis kit comprises an oligonucleotide capable of specifically hybridizing a gene sequence of FARP1 (CD675885.1) in addition to the above 2 kinds of oligonucleotides.

Moreover, for example, the diagnosis kit further comprises oligonucleotides capable of specifically hybridizing at least one gene sequence of 16 genes: ARG1 (NM_000045.2), FARP1 (NM_005766.2), H19 (R83431.1), NULL (BC019018.2), NULL (AW820586.1), NULL (H08012.1), MUC15 (NM_145650.2), HHLA2 (NM_007072.2), SGCD (NM_172244.2), SFRP4 (NM_003014.2), ALOX12 (NM_000697.1), LOC146429 (AL137382.1), PDZRN3 (AL137307.1), NCAM1 (AV702977.1), WNT11 (NM_004626.2), and SORCS2 (NM_020777.1), in addition to the above-mentioned 3 kinds of oligonucleotides.

Moreover, for example, the diagnosis kit further comprises 14 kinds of oligonucleotides capable of specifically hybridizing all of the gene sequences of 16 genes: ARG1 (NM_000045.2), FARP1 (NM_005766.2), H19 (R83431.1), NULL (BC019018.2), NULL (AW820586.1), NULL (H08012.1), MUC15 (NM_145650.2), HHLA2 (NM_007072.2), SGCD (NM_172244.2), SFRP4 (NM_003014.2), ALOX12 (NM_000697.1), LOC146429 (AL137382.1), PDZRN3 (AL137307.1), NCAM1 (AV702977.1), WNT11 (NM_004626.2), and SORCS2 (NM_020777.1) respectively, in addition to the above-mentioned 3 kinds of oligonucleotides.

Here, a mode in which a plurality kinds of oligonucleotides are contained in the diagnosis kit, for example, can be a mode in which these oligonucleotides are collectively contained in one tube, or a mode in which theses oligonucleotides are separately contained in a plurality of tubes. A storage mode of the oligonucleotides in the diagnosis kit, for example, can be a mode in which the oligonucleotides are dissolved in a predetermined solution such as a buffer solution, a mode in which the oligonucleotides are bound to a predetermined carrier, or a mode in which the oligonucleotides are lyophilized to a powder.

Herein, the present invention is not limited to the above-mentioned embodiment, and a variety of modifications are possible without departing from the spirit and scope of the present invention.

For example, according to the embodiment, an assay for assaying an expression amount of a metastasis prediction gene group has been explained as an assay in which an mRNA expression amount of a metastasis prediction gene group is assayed. However, an expression amount of another form of polynucleotides such as a cDNA may be assayed, if an expression amount of a metastasis prediction gene group can be assayed. Further, an expression amount of a protein transcribed from an mRNA of the metastasis prediction gene group may be assayed.

Furthermore, any modification of the above-mentioned methods and a completely different method can be used. The present embodiment only exemplifies an outline of general operational procedures for handling genes.

At present, a full automatic apparatus for sequentially performing extraction, amplification, separation and quantification of nucleotides is commercially available, which is assembled by integrating an electrophoresis apparatus with a PCR apparatus. It is preferable to use this kind of apparatus.

Hereinbefore, the embodiment has been explained as a method commonly including 2 genes: MSR1 (NM_138716.1) and RET (M31213.1) among 19 kinds of the metastasis prediction genes, and a diagnostic kit using the same. However, the spirit and scope of the embodiment further include a method which includes one metastasis prediction gene of the 19 metastasis prediction genes and a diagnosis kit using the same, and a method which includes a metastasis prediction gene group comprising 2 or more kinds of combinations of the 19 metastasis prediction genes and a diagnosis kit using the same.

EXAMPLES

Next, more specific examples of the present invention will be explained as follows.
(Material and Method)
[Microarray Analysis]
According to the present example, firstly, informed consent was obtained from 41 patients diagnosed as the oral cavity cancer; next, a tissue of a lingual cancer was collected from biopsy before small source radiotherapy; and the collected tissue was assayed by a microarray analysis.

Details on the microarray analysis will be explained hereinafter. A collected tissue was directly dipped into RNA later (Ambion Inc., Austin, Tex.). From the dipped tissue, total RNAs were extracted by ISOGEN (Nippon gene) and purified by RNeasy (Qiagen, Hilden, Germany). Biotin-labeled cRNAs were prepared for the purified total RNAs by Codelink Expression Assay Reagent Kit (GE Healthcare, Chandler, Ariz.). The preparation of the biotin-labeled cRNAs was conducted through a preparation process of cDNAs for the total RNAs.

After hybridizing the prepared biotin-labeled cRNAs with Codelink Uniset Human 20K I Bioarray (GE Healthcare, Chandler, Ariz.), the cRNAs were stained by Cy5-Streptavidin and washed by a prescribed washing operation.

Herein, according to Codelink Uniset Human 20K I Bioarray, as disclosed in a gene list provided with the bioarray by the manufacturer, about 20,000 human genes useful for a research field such as a basic research, a biotechnology and a gene-based drug are spotted as oligoprobes, the human genes being selected from genes registered in a public database such as UniGene and Refseq.

Next, an image picture was acquired by Agilent scanner G2505A (Agilent technologies) and a Cy5 fluorescent intensity at each spot in this image picture was counted by using a Codelink Expression 4.0 software (GE Healthcare, Chandler, Ariz.).

This microarray analysis was conducted using two sheets of arrays in each case. Herein, a fluorescent intensity was standardized by a median normalization method in which each fluorescent intensity of each spot is divided by a median of fluorescent intensities of all the spots in the respective arrays, so as to absorb a difference in hybridization among the arrays. Then, an average fluorescent intensity was calculated between the two sheets of arrays using the standardized fluorescent intensity of each spot. This average intensity was used as expression intensity data (expression amount) in the data analysis hereinafter. As a result, in 41 cases of the oral cavity cancer patients, expression intensity data on about 20,000 genes per one case were acquired.

[Selection of Metastasis Prediction Genes and Preparation of Metastasis Discrimination Models Using the Same]

Next, the 41 cases of the oral cavity cancer patients from which the expression intensity data were acquired by the microarray analysis as mentioned above, were classified into groups with and without metastasis. Then, metastasis prediction genes for predicting the metastasis of the oral cavity cancer to the lymph node were selected by using a group (hereinafter, referred as a reference group) including 11 cases with metastasis (metastasis group) and 11 cases without metastasis (non-metastasis group). Further, metastasis discrimination models were prepared, in which the metastasis prediction genes were used.

Here, whether the metastasis occurs or not (which of the metastasis group and the non-metastasis group each case belongs to) was determined by a clinical diagnosis which was conducted after an average of 29 months (from 11 months to 31 months) had passed after small source radiotherapy. Generally, it is suggested that 90% of the metastasis of the oral cavity cancer to the cervical lymph node would occur within 17 months. Therefore, the period (average 29 months) of the present example is enough to determine whether there is metastasis or not. Particularly, 11 cases without metastasis (non-metastasis group) in the reference group are determined that there is no metastasis, even in case of the shortest period, after 32 months passed since the tissue was collected. Accordingly, possibility that the non-metastasis group changes into the metastasis group is quite low after the determination of the non-metastasis group.

First, by comparing the metastasis group with the non-metastasis group in the reference group, 413 genes were extracted in which a ratio of the expression amounts thereof was more than 2 or less than ½. The ratio of the expression amounts corresponds to a value in "Mean ratio (N+ class)/(N− class)" in Table 1 described hereinbefore. If the ratio of the expression amounts between the metastasis group and the non-metastasis group is more than 2 or less than ½, the value is 2 and more or 0.5 and less.

Secondly, was studied a statistically significant difference in the ratio of the expression amounts between the metastasis group and the non-metastasis group, by a permutation test for the extracted 413 genes. Herein, as the certification quantity in the permutation test, a difference between expression amount means of the two groups, $\mu_m - \mu_n$ ($\mu_m$ and $\mu_n$ respectively represent the expression amount mean of the metastasis group and of the non-metastasis group) was used.

In the permutation test, the certification quantity was obtained using a correct label indicating whether there is metastasis or not.

Next, by keeping the total number of the labels indicating whether there is metastasis or not (11 cases with metastasis and 11 cases without metastasis), the label was randomly attached to each sample, and each certification quantity was calculated. In a general permutation test, about 1,000 to 10,000 times labeling is mostly used for random labeling. However, in that case, there are drawbacks that stochastical influence by fluctuation can not be avoided and a p-value varies every calculation. Thus, $_{22}C_{11}=705,432$ times labeling which is the number of all combinations theoretically produced was conducted in the present embodiment.

Then, the p-value was calculated as a ratio of the number of combinations in which a difference between the expression amount means was over the certification quantity, to the total number of combinations, if the certification quantity of the correct label case was a plus value. In contrast, if the certification quantity of the correct label case was a minus value, the p-value was calculated as a ratio of the number of combinations in which a difference between the expression amount means was under the certification quantity, to the total number of combinations.

Accordingly, after selection of genes satisfying the statistical significant difference as p-value <0.01 in the permutation test, 19 genes remained as shown in Table 1. The p-value obtained in the permutation test is shown in a "Permutational p-value" column in Table 1.

Further selection for these 19 genes was performed by leave-one-out cross validation (LOOCV). LOOCV in the embodiment was conducted so as to determine whether a prediction, when one case was removed from the metastasis group or non-metastasis group and the metastasis discrimination model was constructed by the remaining cases, was correctly performed or not; the prediction predicting whether the case that was removed prior to construction of a metastasis discrimination model, belonged to the metastasis group or the non-metastasis group.

Here, when the metastasis discrimination model was constructed, z-score conversion was performed so as to remove effects of an absolute amount of a gene expression amount. The z-score conversion can be performed by subtracting an expression amount mean from each gene expression amount, and dividing a mean difference in subtraction by a standard deviation of each gene expression amount.

A weighted vote analysis was used for the metastasis discrimination model. The weighted vote analysis in the embodiment predicts whether a case "y" in which whether the case belongs to the metastasis group or the non-metastasis group is unknown, belongs to the metastasis group or the non-metastasis group by constructing a model calculating prediction strength (PS) by using the 19 genes selected in the reference group.

First, weight of gene No. i, w (i) was calculated in the weighted vote analysis. The weight w (i) is defined by the following formula.

$$w(i) = \frac{\mu_m(i) - \mu_n(i)}{\sigma_m(i) + \sigma_n(i)} \quad \text{[Formula 1]}$$

Herein, $\mu_m$ and $\mu_n$ respectively refer to an expression amount mean of the metastasis group and that of the non-metastasis group; $\sigma_m$ and $\sigma_n$ are respectively a standard deviation of the metastasis group and that of the non-metastasis group.

Then, an expression pattern of a case in No. j was represented as x (i, j) in Weighted Vote Analysis. PS (j) was calculated by executing weighted votes for the respective genes. PS (j) is defined by the following formula.

$$PS(j) = \frac{\sum_i w_i\left(x(i,j) - \frac{\mu_m(i) + \mu_n(i)}{2}\right)}{\sum_i \left|w_i\left(x(i,j) - \frac{\mu_m(i) + \mu_n(i)}{2}\right)\right|} \cdot 100 \quad \text{[Formula 2]}$$

Further, in selection of genes using LOOCV, a PS difference between the metastasis group and the non-metastasis group was evaluated; the difference being calculated by data of the reference group in LOOCV. The evaluation was used as an index of performance of the metastasis discrimination model.

The following four models were used in the gene selection steps.

Model 1: A gene having the smallest p value in a permutation test was added sequentially to the model. A PS difference between the two groups was evaluated in a t-test.

Model 2: A gene having the smallest p value in a permutation test was added sequentially to the model. A PS difference between the two groups was evaluated in the Wilcoxon test.

Model 3: A gene having the smallest p value in a permutation test was used as an initial model, and a gene having the most improved result was added sequentially to the model. A PS difference between the two groups was evaluated in a t-test.

Model 4: A gene having the smallest p value in a permutation test was used as an initial model, and a gene having the most improved result was added sequentially to the model. A PS difference between the two groups was evaluated in the Wilcoxon test.

[Determination of Metastasis Discrimination Models Using Selected Metastasis Prediction Genes]

Prediction strength of the metastasis discrimination model using the selected metastasis prediction genes was determined by using a group (hereinafter, referred as a test group) which was independent of the reference group including 8 metastasis cases (a metastasis group) and 11 no metastasis cases (a non-metastasis group) out of 41 cases of oral cavity cancer patients for which microarray assays were conducted.

Z-score conversion was performed so as to remove effects of an absolute amount of a gene expression amount in application of test group data to a weighted vote analysis (WVA). The z-score conversion can be performed by subtracting an expression amount mean from each gene expression amount every case in the test group, and dividing a difference in subtraction by a standard deviation of each gene expression amount. Herein, the same expression amount mean and standard deviation as used in the z-score conversion for the reference group were used.

<Results>

Table 2 shows results in the metastasis prediction for the test group performed by the metastasis discrimination model using all of the 19 genes in the metastasis prediction gene group.

TABLE 2

|  | Metastasis | Case No. | MSR1 GE57055 NM_138715.1 | ARG1 GE59705 NM_000045.2 | NULL GE62837 BC019018.2 | MUC15 GE80513 NM_145650.2 | SGCD GE80907 NM_172244.2 | ALOX12 GE80938 NM_000697.1 | SFRP4 GE81222 NM_003014.2 |
|---|---|---|---|---|---|---|---|---|---|
| Test | + | 936 | −0.14481 | −0.65758 | −1.2754 | −0.85093 | −0.22555 | −0.09091 | −0.62793 |
|  | + | 1479 | −0.51829 | 0.187536 | −0.9382 | −0.7226 | −0.52149 | −0.21182 | 0.27451 |
|  | + | 1572 | −0.57473 | 18.46256 | −0.9105 | 5.144646 | −0.69416 | 0.056714 | −0.35647 |

TABLE 2-continued

| Metastasis | Case No. | | | | | | |
|---|---|---|---|---|---|---|---|
| + | 1578 | 0.830464 | 0.624915 | -0.9329 | 0.377735 | -0.29583 | 0.306057 | 1.00798 |
| + | 1665 | 1.645579 | -0.58688 | -0.0978 | -0.37019 | 1.69047 | -0.74029 | 1.95234 |
| + | 1668 | 2.158406 | -0.69395 | -0.2599 | -0.64121 | -0.74094 | -0.62815 | -0.33048 |
| + | 1670 | 1.262855 | -0.05495 | -1.1836 | 1.954669 | 0.05722 | -0.60119 | -0.29344 |
| + | 1671 | 0.102372 | -0.58148 | -1.2363 | -0.55712 | 0.58709 | -0.86513 | 1.48613 |
| − | 1477 | -0.44874 | -0.05842 | -1.0894 | 0.12708 | -0.99262 | 0.188404 | -0.6138 |
| − | 1478 | 0.604981 | 0.604615 | 0.70681 | 0.475917 | -0.85923 | 0.591885 | -0.69391 |
| − | 1480 | 0.037288 | 0.502834 | -0.3576 | -0.19539 | -0.20245 | -0.67205 | -0.03487 |
| − | 1482 | -0.4574 | 1.399825 | -0.7679 | 0.152922 | 0.18664 | 2.485555 | 0.27761 |
| − | 1571 | 0.253298 | 3.094357 | -0.806 | 0.84707 | -0.68926 | -0.49288 | -0.72826 |
| − | 1573 | -0.60097 | -0.46827 | -1.1922 | 0.560073 | -0.93251 | -0.35356 | -0.68826 |
| − | 1576 | -0.18905 | -0.6211 | -0.9494 | -0.9911 | -0.18588 | -0.62674 | 0.3167 |
| − | 1666 | -0.308 | -0.57666 | -1.0801 | 0.367222 | -0.38184 | -0.26824 | -0.57599 |
| − | 1667 | 0.354305 | -0.68375 | 0.81781 | -0.62704 | -0.76608 | -0.64953 | -0.40288 |
| − | 1672 | -0.34577 | -0.49904 | -1.1771 | 2.484135 | -0.90455 | 1.603443 | -0.7745 |
| − | 1673 | -1.01533 | 2.130662 | -1.348 | 1.666055 | -0.0688 | -0.62633 | 0.2265 |

| | Metastasis | Case No. | WNT11 GE81421 NM_004626.2 | FARP1 GE81559 NM_005788.2 | HHLA2 GE81723 NM_007072.2 | RET GE82572 M31213.1 | PDZRN3 GE84465 AL137307.1 | NCAM1 GE85957 AV702977.1 | H19 GE87260 R83431.1 |
|---|---|---|---|---|---|---|---|---|---|
| Test | + | 936 | 13.8008 | -0.13839 | -0.84432 | 1.99943 | -1.0282 | -0.8536 | -0.647 |
| | + | 1479 | -0.1715 | -0.24825 | -0.53831 | 0.08397 | -0.6721 | -0.868 | -0.639 |
| | + | 1572 | 8.46771 | -0.65544 | 1.13596 | -0.4842 | -0.7621 | -0.8816 | -0.2515 |
| | + | 1578 | 13.3507 | -0.75562 | -0.05099 | -0.3212 | -0.3126 | -0.3243 | -0.6609 |
| | + | 1665 | 2.37915 | 0.722219 | -0.1419 | -0.3129 | -0.6706 | 0.69446 | -0.3823 |
| | + | 1668 | -0.00739 | 1.12547 | -0.16178 | -0.6126 | -0.3345 | -0.6257 | -0.5103 |
| | + | 1670 | 3.26799 | -0.26927 | -0.87459 | -0.7063 | -0.8726 | -0.7138 | 0.5585 |
| | + | 1671 | 1.32052 | -0.12749 | -0.84225 | -0.2582 | 0.47761 | -0.6715 | 0.6203 |
| | − | 1477 | -0.47823 | -1.3386 | -0.20985 | -0.4054 | -0.4848 | -0.8123 | -0.7355 |
| | − | 1478 | -0.23921 | -1.19729 | -0.52622 | -0.7022 | 0.54155 | 0.11151 | -0.9161 |
| | − | 1480 | -0.48056 | -0.05105 | 1.109847 | -0.6989 | -0.8669 | -0.4388 | 0.43195 |
| | − | 1482 | 0.98245 | -0.02535 | 0.979228 | -0.9428 | 1.24807 | -0.9052 | -0.4917 |
| | − | 1571 | -0.04763 | 0.371817 | -0.29635 | -0.5855 | -0.6879 | -0.7878 | -0.4294 |
| | − | 1573 | -0.52736 | -1.25502 | 1.430914 | -0.4794 | -0.1429 | -0.7697 | -0.4083 |
| | − | 1576 | -0.50465 | 0.304088 | -0.31539 | 4.06692 | 1.42097 | 1.73796 | -0.4677 |
| | − | 1666 | -0.43623 | -0.7322 | 0.453701 | -0.6247 | -0.0736 | -0.3561 | -0.3736 |
| | − | 1667 | -0.3709 | 0.6579 | 0.166925 | -0.6082 | 0.37112 | -0.6773 | -0.6497 |
| | − | 1672 | -0.13126 | -1.27799 | -0.84511 | -0.709 | 0.36111 | -0.833 | -0.5636 |
| | − | 1673 | -0.88492 | -0.69102 | -0.48905 | -1.0546 | -1.1759 | -0.9632 | -0.4885 |

| | Metastasis | Case No. | NULL GE87320 H08012.1 | NULL GE87326 AW820588.1 | SORCS2 GE88732 NM_020777.1 | LOC146429 GE88740 AL137382.1 | FARP1 GE88809 NM_005766.2 | Prediction Strength | Judgment |
|---|---|---|---|---|---|---|---|---|---|
| Test | + | 936 | -0.34729 | 0.27678 | -0.61211 | -0.64704 | 0.287502 | 63.92 | + |
| | + | 1479 | -0.33205 | -0.6687 | 0.49969 | 0.755973 | -0.41734 | -38.70 | − |
| | + | 1572 | -0.31488 | -0.3266 | 0.13622 | -0.5075 | -0.4019 | -58.39 | − |
| | + | 1578 | -0.28843 | -0.2577 | -0.35786 | 0.147065 | -0.91524 | 36.01 | + |
| | + | 1665 | -0.19867 | 1.21567 | 0.01535 | -0.72255 | 1.235589 | 87.46 | + |
| | + | 1668 | -0.33091 | 1.1465 | -0.36983 | -0.50505 | 0.587006 | 42.68 | + |
| | + | 1670 | -0.26403 | -0.4278 | -0.33905 | -0.53823 | 0.253499 | 19.49 | + |
| | + | 1671 | -0.20739 | 1.11402 | 0.24587 | -0.67406 | 0.34455 | 51.30 | + |
| | − | 1477 | -0.33424 | -1.1768 | 0.0449 | 0.032756 | -1.15711 | -86.62 | − |
| | − | 1478 | -0.2896 | -1.2869 | -0.61671 | 4.72451 | -1.22599 | -82.18 | − |
| | − | 1480 | -0.25323 | -0.3298 | -0.46019 | -0.66296 | 0.266765 | -25.98 | − |
| | − | 1482 | -0.26697 | -0.0984 | -0.47095 | -0.35954 | 0.782629 | -60.13 | − |
| | − | 1571 | -0.33652 | -0.8817 | 0.13599 | -0.64975 | 0.765277 | -42.36 | − |
| | − | 1573 | -0.32223 | -1.0289 | -0.62741 | -0.15807 | -1.44648 | -83.84 | − |
| | − | 1576 | -0.18942 | 1.02847 | 0.1397 | -0.54472 | 0.225746 | 55.70 | + |
| | − | 1666 | -0.28201 | -0.7195 | -0.50939 | -0.38067 | -0.98753 | -73.40 | − |
| | − | 1667 | -0.36348 | 0.34067 | -0.24903 | -0.65023 | 0.100796 | 6.45 | + |
| | − | 1672 | -0.32633 | -1.2068 | -0.4882 | 0.816163 | -1.23216 | -83.01 | − |
| | − | 1673 | -0.43321 | -0.4798 | -0.62471 | -0.67964 | -0.56587 | -63.82 | − |

In Table 2, the weighted votes calculated are listed for every metastasis prediction gene in each case (indicated as a case number). Base on these values, prediction strength (PS) of each case is listed in a "prediction strength" column. Herein, a case having PS of + value represents a case in which it was predicted that an oral cavity cancer metastasized to a cervical lymph node. A case having PS of − value represents a case in which it was predicted that an oral cavity cancer did not metastasize to a cervical lymph node. The larger the absolute value of PS is, the more the predicted probability of metastasis or non-metastasis increases.

Further, in Table 2, a result obtained by comparing the above-mentioned data predicted by PS with actual data is shown in a "Judgment" column; the actual data that which of a metastasis group (+ in a "metastasis" column) and a non-metastasis group (− in a "metastasis" column) each case is actually classified to. If a symbol of "Judgment" is +, this is a case of which prediction was performed correctly. On the other hand, if the symbol of "Judgment" is −, this is a case of which prediction was not performed correctly.

Hereby, if the 19 genes were used, metastasis prediction for 6 cases out of 8 cases in a metastasis group and metastasis prediction for 9 cases out of 11 cases in a non-metastasis group were correctly performed (correct prediction ratio of 79% (15/19)). Sensitivity and specificity values were 0.750 and 0.818 respectively.

In this way, 4 genes (MSR1, RET, FARP1, and ARG1) were selected by a gene selection in Model 1. Metastasis prediction for the test group was performed by the metastasis discrimination model using the 4 genes. As a result, prediction for 6 cases out of 8 cases in the metastasis group and prediction for 9 cases out of 11 cases in the non-metastasis group were correctly performed (correct prediction ratio of 79% (15/19)). Sensitivity and specificity values were 0.750 and 0.818 respectively.

Next, 2 genes (MSR1 and RET) were selected by a gene selection in Model 2. Metastasis prediction for the test group was performed by the metastasis discrimination model using the 2 genes. As a result, prediction for 5 cases out of 8 cases in the metastasis group and prediction for 10 cases out of 11 cases in the non-metastasis group were correctly performed (correct prediction ratio of 79% (15/19)). Sensitivity and specificity values were 0.625 and 0.909 respectively.

Next, 3 genes (MSR1, RET and ARG1) were selected by a gene selection in Model 3. Metastasis prediction for the test group was performed by the metastasis discrimination model using the 3 genes. As a result, prediction for 6 cases out of 8 cases in the metastasis group and prediction for 9 cases out of 11 cases in the non-metastasis group were correctly performed (correct prediction ratio of 79% (15/19)). Sensitivity and specificity values were 0.750 and 0.818 respectively.

Next, 2 genes (MSR1 and RET) were selected by a gene selection in Model 4, similarly to Model 2. Metastasis prediction for the test group was performed by the metastasis discrimination model using the 2 genes. As a result, prediction for 5 cases out of 8 cases in the metastasis group and prediction for 10 cases out of 11 cases in the non-metastasis group, were correctly performed (correct prediction ratio of 79% (15/19)). Sensitivity and specificity values were 0.625 and 0.909 respectively.

The results mentioned above will be explained referring to FIG. 1 to FIG. 3 easily to be understood visually. Here, in FIG. 1 to FIG. 3, the number of the results is not the same as the number of the case in the plot because some closely neighboring plots overlap each other.

Figure 1:
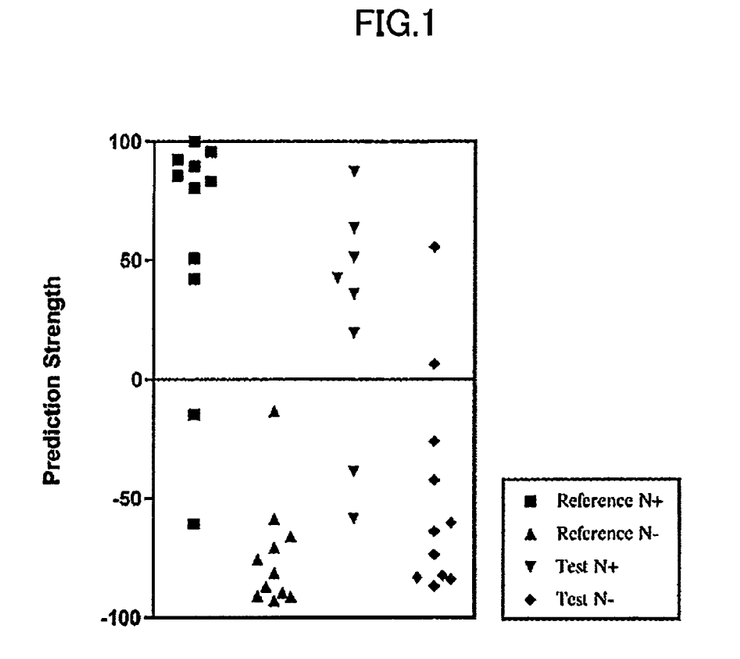
FIG. 1 shows a result in predicting metastasis of a test group using all of 19 genes of a metastasis prediction gene group.

FIG. 1 shows the result of metastasis prediction for the test group by using all of the 19 genes in the metastasis prediction gene group. In FIG. 1, Test N+ (▼) in a third column from the left of a horizontal axis represents a metastasis group of the test group. Test N− (♦) in a fourth column from the left of the horizontal axis represents a non-metastasis group of the test group. A first column and a second column from the left of the horizontal axis represent a reference group. Reference N+ (■) in the first column represents the metastasis group, and Reference N− (▲) represents the non-metastasis group. Prediction strength in each case is plotted on a vertical axis. As shown in FIG. 1, a case having high prediction strength calculated for the test group corresponded to a metastasis group, and a case having low prediction strength calculated for the test group corresponded to a non-metastasis group. As mentioned above, the correct prediction ratio was 79% (15/19).

Figure 2:
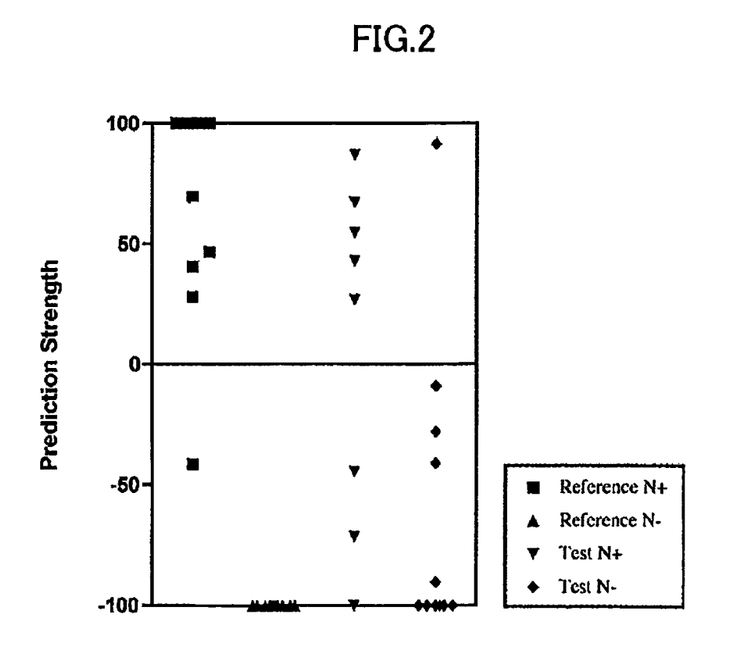
FIG. 2 shows a result in predicting the metastasis of a test group using 2 genes (MSR1 and RET) commonly selected in Models 1 to 4 from the metastasis prediction gene group.

FIG. 2 shows the result of metastasis prediction for the test group by using the commonly selected 2 genes in Models 1 to 4 (MSR1 and RET) in the metastasis prediction gene group. A horizontal axis and a vertical axis in FIG. 2 are the same as those in FIG. 1. As shown in FIG. 2, a case having high prediction strength calculated for the test group corresponded to the metastasis group, and a case having low prediction strength calculated for the test group corresponded to the non-metastasis group. As mentioned above, the correct prediction ratio was 79% (15/19).

Figure 3:
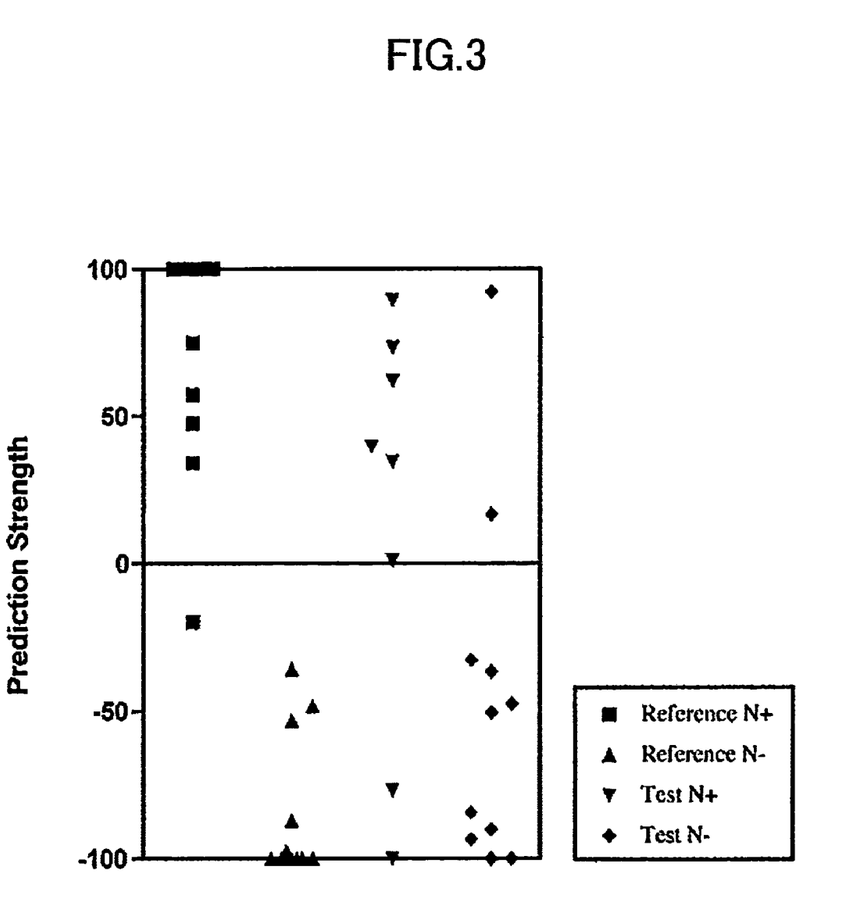
FIG. 3 shows a result in predicting the metastasis of a test group using 3 genes (MSR1, RET and ARG1) commonly selected in Models 1 and 3 from the metastasis prediction gene group.

FIG. 3 shows the result of metastasis prediction for the test group by using the commonly selected 3 genes in Models 1 and 3 (MSR1, RET and ARG1) in the metastasis prediction gene group. A horizontal axis and a vertical axis in FIG. 3 are the same as those in FIG. 1. As shown in FIG. 3, a case having high prediction strength calculated for the test group corresponded to the metastasis group, and a case having low prediction strength calculated for the test group corresponded to the non-metastasis group. As mentioned above, the correct prediction ratio was 79% (15/19).

Thus described, according to the embodiment, a metastasis prediction result using all of the 19 genes was almost identical to metastasis prediction results using Models 1 to 4. Further, in every case, metastasis prediction was performed in a high correct prediction ratio. Therefore, it is concluded that all of these groups: the 2 genes group (MSR1 and RET), the 3 genes group (MSR1, RET, and ARG1), the 4 genes group (MSR1, RET, FARP1, and ARG1), and the 19 genes group are useful for predicting whether or not there is the metastasis of the oral cavity cancer.

We claim:

1. A method for predicting metastasis of an oral cavity cancer to a cervical lymph node, the method comprising:
   assaying expression amounts of a metastasis prediction gene group in which the expression amounts are changed between a metastasis group indicating that the oral cavity cancer metastasizes to the cervical lymph node and a non-metastasis group indicating that the oral cavity cancer does not metastasize to the cervical lymph node, based on a sample collected from a primary lesion of the oral cavity cancer;
   predicting a probability that the oral cavity cancer metastasizes to the cervical lymph node by comparing the expression amounts of the metastasis prediction gene group with the expression amounts of metastasis prediction genes in the metastasis group and/or the non-metastasis group; wherein
   the metastasis prediction gene group includes 2 genes: MSR1 (NM_138716.1) and RET (M31213.1).

2. The method for predicting the metastasis of the oral cavity cancer to the cervical lymph node according to claim 1, wherein the metastasis prediction gene group further includes a gene of FARP1 (CD675885.1).

3. The method for predicting the metastasis of the oral cavity cancer to the cervical lymph node according to claim 2, wherein the metastasis prediction gene group further includes at least one of 16 genes: ARG1 (NM_000045.2), FARP1 (NM_005766.2), H19 (R83431.1), NULL (BC019018.2), NULL (AW820586.1), NULL (H08012.1), MUC15 (NM_145650.2), HHLA2 (NM_007072.2), SGCD (NM_172244.2), SFRP4 (NM_003014.2), ALOX12 (NM_000697.1), LOC146429 (AL137382.1), PDZRN3 (AL137307.1), NCAM1 (AV702977.1), WNT11 (NM_004626.2) and SORCS2 (NM_020777.1).

4. The method for predicting the metastasis of the oral cavity cancer to the cervical lymph node according to claim 2, wherein the metastasis prediction gene group further includes all of the 16 genes: ARG1 (NM_000045.2), FARP1 (NM_005766.2), H19 (R83431.1), NULL (BC019018.2), NULL (AW820586.1), NULL (H08012.1), MUC15 (NM_145650.2), HHLA2 (NM_007072.2), SGCD (NM_172244.2), SFRP4 (NM_003014.2), ALOX12 (NM_000697.1), LOC146429 (AL137382.1), PDZRN3 (AL137307.1), NCAM1 (AV702977.1), WNT11 (NM_004626.2) and SORCS2 (NM_020777.1).

5. A diagnosis kit for predicting metastasis of an oral cavity cancer to a cervical lymph node, the diagnosis kit comprising 2 kinds of oligonucleotides specifically hybridizing to 2 gene sequences of MSR1 (NM__138716.1) and RET (M31213.1), respectively: MSR1 (NM__138716.1) and RET (M31213.1) being metastasis prediction genes, wherein
the diagnosis kit is configured to perform:
assaying expression amounts of the metastasis prediction genes in which the expression amounts are changed between a metastasis group indicating that the oral cavity cancer metastasizes to the cervical lymph node and a non-metastasis group indicating that the oral cavity cancer does not metastasize to the cervical lymph node, based on a sample collected from a primary lesion of the oral cavity cancer; and
predicting a probability that the oral cavity cancer metastasizes to the cervical lymph node by comparing the expression amounts of the metastasis prediction genes with the expression amounts of metastasis prediction genes in the metastasis group and/or the non-metastasis group.

6. The diagnosis kit for predicting the metastasis of the oral cavity cancer to the cervical lymph node according to claim 5, wherein the diagnosis kit further comprises oligonucleotide specifically hybridizing to a gene sequence of FARP1 (CD675885.1) which is a metastasis prediction gene.

7. The diagnosis kit for predicting the metastasis of the oral cavity cancer to the cervical lymph node according to claim 6, wherein the diagnosis kit further comprises one or more oligonucleotides specifically hybridizing to at least one gene sequence of 16 genes, respectively: ARG1 (NM__000045.2), FARP1 (NM__005766.2), H19 (R83431.1), NULL (BC019018.2), NULL (AW820586.1), NULL (H08012.1), MUC15 (NM__145650.2), HHLA2 (NM__007072.2), SGCD (NM__172244.2), SFRP4 (NM__003014.2), ALOX12 (NM__000697.1), LOC146429 (AL137382.1), PDZRN3 (AL137307.1), NCAM1 (AV702977.1), WNT11 (NM__004626.2) and SORCS2 (NM__020777.1) which are metastasis prediction genes.

8. The diagnosis kit for predicting the metastasis of the oral cavity cancer to the cervical lymph node according to claim 6, wherein the diagnosis kit further comprises 16 kinds of oligonucleotides specifically hybridizing to all of the 16 genes, respectively: ARG1 (NM__000045.2), FARP1 (NM__005766.2), H19 (R83431.1), NULL (BC019018.2), NULL (AW820586.1), NULL (H08012.1), MUC15 (NM__145650.2), HHLA2(NM__007072.2), SGCD (NM__172244.2), SFRP4 (NM__003014.2), ALOX12 (NM__000697.1), LOC146429 (AL137382.1), PDZRN3 (AL137307.1), NCAM1 (AV702977.1), WNT11 (NM__004626.2) and SORCS2 (NM__020777.1) which are metastasis prediction genes.

* * * * *